US011427834B2

(12) United States Patent
Li et al.

(10) Patent No.: US 11,427,834 B2
(45) Date of Patent: Aug. 30, 2022

(54) **PROTEIN FOR REGULATING INSECT RESISTANCE IN *ARABIDOPSIS THALIANA* AND ENCODING GENE AND USE THEREOF**

(71) Applicant: Plant Protection Research Institute, Guangdong Academy of Agricultural Sciences, Guangdong (CN)

(72) Inventors: Yifeng Li, Guangdong (CN); Zhenfei Zhang, Guangdong (CN); Chun Chen, Guangdong (CN); Longyu Yuan, Guangdong (CN)

(73) Assignee: PLANT PROTECTION RESEARCH INSTITUTE, GUANGDONG ACADEMY OF AGRICULTURAL SCIENCES, Guangdong (CN)

(*) Notice: Subject to any disclaimer, the term of this patent is extended or adjusted under 35 U.S.C. 154(b) by 0 days.

(21) Appl. No.: 16/941,345

(22) Filed: Jul. 28, 2020

(65) Prior Publication Data

US 2021/0130836 A1 May 6, 2021

(30) Foreign Application Priority Data

Oct. 31, 2019 (CN) ........................ 201911049321.X

(51) Int. Cl.
*C12N 15/82* (2006.01)
*C12N 9/12* (2006.01)

(52) U.S. Cl.
CPC ........... *C12N 15/8286* (2013.01); *C12N 9/12* (2013.01); *C12N 15/8213* (2013.01); *C12N 15/8218* (2013.01); *C12Y 207/11001* (2013.01)

(58) Field of Classification Search
None
See application file for complete search history.

(56) References Cited

U.S. PATENT DOCUMENTS

2013/0096032 A1* 4/2013 Bush .................... C12Q 1/6895 506/16

OTHER PUBLICATIONS

Tair, https://www.arabidopsis.org/servlets/TairObject?type=locus&name=at5g10530, accessed Aug. 19, 2021.*
Wang et al (2015, MPMI 28:1032-1048).*
Tabata et al., 2021, UniProtKB/Swiss-Prot Accesasion No. Q9LXA5, https://www.ncbi.nlm.nih.gov/protein/Q9LXA5.*
Alonso et al (2003, Science 301:653-657).*
Wang et al (2014, MPMI 12:1390-1402).*
Underwood et al (2006, Gen Bank Accession No. DQ446940, https://www.ncbi.nlm.nih.gov/nuccore/DQ446940).*

* cited by examiner

*Primary Examiner* — Anne Kubelik
(74) *Attorney, Agent, or Firm* — D'Ambrosio & Menon, PLLC; Usha Menon

(57) ABSTRACT

The present disclosure relates to use of a lectin receptor-like kinase LecRK-IX.1 as a protein for regulating insect resistance of *Arabidopsis thaliana*. *A. thaliana* with high resistance to *Bemisia tabaci* can be cultivated by reducing the expression of, or knocking out, an encoding gene of the protein. Therefore, *Arabidopsis thaliana* with the high-level resistance to *Bemisia tabaci* can be cultivated. The gene and its encoded protein can be applied to plant genetic improvement.

1 Claim, No Drawings

Specification includes a Sequence Listing.

SEQUENCE LISTING

<160> NUMBER OF SEQ ID NOS: 5

<210> SEQ ID NO 1
<211> LENGTH: 1956
<212> TYPE: DNA
<213> ORGANISM: Arabidopsis thaliana

<400> SEQUENCE: 1

| | | | | | | |
|---|---|---|---|---|---|---|
| atggccaact | caattctgtt | attttccttt | gttttggttc | tccctttttgt | ctgttcagtt | 60 |
| caatttaaca | tatctcgttt | tggatcagat | gtttctgaaa | tagcatacca | aggagatgca | 120 |
| agagcaaatg | gggctgttga | gcttaccaac | attgactaca | catgccgtgc | cggttgggct | 180 |
| acttatggta | agcaggttcc | tttatggaat | ccaggtacca | gtaagccttc | ggattttagt | 240 |
| acgcgtttct | ccttcagaat | tgatacccgt | aatgttgggt | atggtaatta | cggtcatggg | 300 |
| tttgctttct | ttctagctcc | agcgagaatc | caattgcctc | ccaactcagc | tggtggtttc | 360 |
| ttgggtctat | tcaatggaac | caataatcag | tcttctgctt | tcccacttgt | ttatgtcgag | 420 |
| ttcgacacat | ttactaatcc | agaatgggat | cctctcgatg | tcaaatccca | tgtaggaatc | 480 |
| aacaacaact | ctcttgtttc | ttctaactac | acttcttgga | atgcaacgtc | acacaaccaa | 540 |
| gatataggcc | gtgtcctgat | attctatgat | tccgctagaa | gaaacttgag | tgtctcttgg | 600 |
| acttacgact | taacatctga | tcctctggag | aattcaagcc | tatcttacat | cattgatctc | 660 |
| tcaaaggtac | tgccatcaga | agttacaatt | gggttttctg | cgacatctgg | agggtcacc | 720 |
| gagggaaata | gacttctgtc | atgggagttc | agttcaagcc | tggagctaat | agatataaag | 780 |
| aaaagtcaga | atgacaagaa | ggggatgata | attggtattt | cagtttctgg | gttcgttttg | 840 |
| ctgaccttt | ttattacctc | gctcatcgtc | ttcttgaaac | ggaagcagca | gaagaagaaa | 900 |
| gcagaggaga | cagaaaactt | aacatcgata | atgaagatc | tcgaaagagg | agcaggacca | 960 |
| agaaagttta | cttataaaga | tcttgcatca | gctgcaaaca | atttcgcaga | tgataggaag | 1020 |
| ctaggggaag | gagggtttgg | agcggtttat | agagggtact | taaacagctt | agatatgatg | 1080 |
| gttgcgataa | agaagtttgc | gggtgggtct | aagcagggaa | aaagagagtt | cgtaaccgaa | 1140 |
| gtaaagataa | tcagcagttt | gagacatcga | aaccttgtgc | aactcattgg | ttggtgccat | 1200 |
| gagaaagatg | agtttctaat | gatatacgag | ttcatgccaa | atggtagcct | tgacgcccat | 1260 |
| ctatttggta | aaaagccgca | tctcgcttgg | catgtgagat | gcaaaataac | tctcggtctc | 1320 |
| gcctctgcac | tgctttatct | tcacgaggag | tgggagcagt | gtgttgtaca | cagagacatc | 1380 |
| aaggcgagta | atgtgatgct | cgactccaat | ttcaatgcca | agcttggtga | tttcgggttg | 1440 |
| gctagattga | tggaccacga | gctaggtcca | cagactacag | ggttagcagg | aacatttggt | 1500 |
| tacatggctc | ctgaatacat | aagcaccgga | agggcgagca | agaatctga | tgtgtatagc | 1560 |
| tttggagtgg | ttacattaga | gattgttaca | ggaagaaaat | ctgtggatcg | aagacaagga | 1620 |
| agagtagagc | ctgtaacaaa | ccttgtagag | aaaatgtggg | acctttatgg | aaaaggagaa | 1680 |
| gttattacag | ctatcgacga | gaaactcagg | atcggtggtt | tcgatgagaa | acaagcagaa | 1740 |
| tgtctcatga | ttgtaggatt | atggtgtgct | catcctgatg | taaacacgag | gccttcaata | 1800 |
| aaacaagcaa | tccaagtctt | gaatcttgaa | gcaccagtgc | ctcatcttcc | gaccaaaatg | 1860 |
| cctgtcgcaa | catatcatgt | atcctcttcg | aatactacat | cggtaagctc | tggtggagct | 1920 |
| acggtaacgt | tttcaagtgc | tcaacatggt | cgttga | | | 1956 |

<210> SEQ ID NO 2
<211> LENGTH: 20

```
<212> TYPE: DNA
<213> ORGANISM: Artificial Sequence
<220> FEATURE:
<223> OTHER INFORMATION: gRNA sequence 1
<220> FEATURE:
<221> NAME/KEY: misc_feature
<222> LOCATION: (1)..(20)

<400> SEQUENCE: 2
tccgaaggct tactggtacc                                          20

<210> SEQ ID NO 3
<211> LENGTH: 23
<212> TYPE: DNA
<213> ORGANISM: Artificial Sequence
<220> FEATURE:
<223> OTHER INFORMATION: Target sequence 1
<220> FEATURE:
<221> NAME/KEY: misc_feature
<222> LOCATION: (1)..(23)

<400> SEQUENCE: 3
tccgaaggct tactggtacc tgg                                      23

<210> SEQ ID NO 4
<211> LENGTH: 25
<212> TYPE: DNA
<213> ORGANISM: Artificial Sequence
<220> FEATURE:
<223> OTHER INFORMATION: Hyg-f
<220> FEATURE:
<221> NAME/KEY: misc_feature
<222> LOCATION: (1)..(25)

<400> SEQUENCE: 4
acggtgtcgt ccatcacagt ttgcc                                    25

<210> SEQ ID NO 5
<211> LENGTH: 24
<212> TYPE: DNA
<213> ORGANISM: Artificial Sequence
<220> FEATURE:
<223> OTHER INFORMATION: Hyg-r
<220> FEATURE:
<221> NAME/KEY: misc_feature
<222> LOCATION: (1)..(24)

<400> SEQUENCE: 5
ttccggaagt gcttgacatt ggga                                     24
```

PROTEIN FOR REGULATING INSECT RESISTANCE IN *ARABIDOPSIS THALIANA* AND ENCODING GENE AND USE THEREOF

CROSS-REFERENCE TO RELATED APPLICATIONS

This application is based on and claims the benefit of priority from Chinese Patent Application No. 201911049321.X, filed on Oct. 31, 2019, the entirety of which is incorporated by reference herein.

INCORPORATION BY REFERENCE

This application includes a sequence listing in computer readable form (a "txt" file) that is submitted herewith. This sequence listing is incorporated by reference herein as (SEQ ID NO: 1)
ATGGCCAACTCAATTCTGTTATTTTCCTTTGTTTGGTTCTCCCTTTTGT

CTGTTCAGTTCAATTTAACATATCTCGTTTTGGATCAGATGTTTCTGAAA

TAGCATACCAAGGAGATGCAAGAGCAAATGGGGCTGTTGAGCTTACCAAC

ATTGACTACACATGCCGTGCCGGTTGGGCTACTTATGGTAAGCAGGTTCC

TTTATGGAATCCAGGTACCAGTAAGCCTTCGGATTTTAGTACGCGTTTCT

CCTTCAGAATTGATACCCGTAATGTTGGGTATGGTAATTACGGTCATGGG

TTTGCTTTCTTTCTAGCTCCAGCGAGAATCCAATTGCCTCCCAACTCAGC

TGGTGGTTTCTTGGGTCTATTCAATGGAACCAATAATCAGTCTTCTGCTT

TCCCACTTGTTTATGTCGAGTTCGACACATTTACTAATCCAGAATGGGAT

CCTCTCGATGTCAAATCCCATGTAGGAATCAACAACAACTCTCTTGTTTC

TTCTAACTACACTTCTTGGAATGCAACGTCACACAACCAAGATATAGGCC

GTGTCCTGATATTCTATGATTCCGCTAGAAGAAACTTGAGTGTCTCTTGG

ACTTACGACTTAACATCTGATCCTCTGGAGAATTCAAGCCTATCTTACAT

CATTGATCTCTCAAAGGTACTGCCATCAGAAGTTACAATTGGGTTTTCTG

CGACATCTGGAGGGGTCACCGAGGGAAATAGACTTCTGTCATGGGAGTTC

AGTTCAAGCCTGGAGCTAATAGATATAAAGAAAAGTCAGAATGACAAGAA

GGGGATGATAATTGGTATTTCAGTTTCTGGGTTCGTTTTGCTGACCTTTT

TTATTACCTCGCTCATCGTCTTCTTGAAACGGAAGCAGCAGAAGAAGAAA

GCAGAGGAGACAGAAAACTTAACATCGATAAATGAAGATCTCGAAAGAGG

AGCAGGACCAAGAAAGTTTACTTATAAAGATCTTGCATCAGCTGCAAACA

ATTTCGCAGATGATAGGAAGCTAGGGGAAGGAGGGTTTGGAGCGGTTTAT

AGAGGGTACTTAAACAGCTTAGATATGATGGTTGCGATAAAGAAGTTTGC

GGGTGGGTCTAAGCAGGGAAAAAGAGAGTTCGTAACCGAAGTAAAGATAA

TCAGCAGTTTGAGACATCGAAACCTTGTGCAACTCATTGGTTGGTGCCAT

GAGAAAGATGAGTTTCTAATGATATACGAGTTCATGCCAAATGGTAGCCT

TGACGCCCATCTATTTGGTAAAAAGCCGCATCTCGCTTGGCATGTGAGAT

GCAAAATAACTCTCGGTCTCGCCTCTGCACTGCTTTATCTTCACGAGGAG

TGGGAGCAGTGTGTTGTACACAGAGACATCAAGGCGAGTAATGTGATGCT

CGACTCCAATTTCAATGCCAAGCTTGGTGATTTCGGGTTGGCTAGATTGA

-continued

TGGACCACGAGCTAGGTCCACAGACTACAGGGTTAGCAGGAACATTTGGT

TACATGGCTCCTGAATACATAAGCACCGGAAGGGCGAGCAAAGAATCTGA

TGTGTATAGCTTTGGAGTGGTTACATTAGAGATTGTTACAGGAAGAAAAT

CTGTGGATCGAAGACAAGGAAGAGTAGAGCCTGTAACAAACCTTGTAGAG

AAAATGTGGGACCTTTATGGAAAAGGAGAAGTTATTACAGCTATCGACGA

GAAACTCAGGATCGGTGGTTTCGATGAGAAACAAGCAGAATGTCTCATGA

TTGTAGGATTATGGTGTGCTCATCCTGATGTAAACACGAGGCCTTCAATA

AAACAAGCAATCCAAGTCTTGAATCTTGAAGCACCAGTGCCTCATCTTCC

GACCAAAATGCCTGTCGCAACATATCATGTATCCTCTTCGAATACTACAT

CGGTAAGCTCTGGTGGAGCTACGGTAACGTTTTCAAGTGCTCAACATGGT

CGTTGA

TECHNICAL FIELD

The present disclosure relates to the field of molecular biology, particularly to a protein for regulating insect resistance in *Arabidopsis thaliana*, and the encoding gene and uses thereof.

BACKGROUND

*Bemisia tabaci* (Gennadius) is a worldwide insect pest, and distributes in all continents except Antarctica. *B. tabaci* has an extremely wide host range and attacks substantially all tropical and temperate crops, resulting in serious harm. It has high population density and food intake. During sucking up host plant juices, *B. tabaci* produces a lot of honeydew, which can induce sooty molds and then seriously affect crop photosynthesis. In addition, *B. tabaci* is a main vector of various plant viruses, which will cause deformity, atrophy, chlorotic leaves, and wilting in host plants. It is one of the most harmful invasive species in the world, and causes destructive damages to important crops in many countries and regions during the invasion.

Though chemical control of *B. tabaci* has been effective to some extent (except in severe outbreak years), it has a high economic and ecological cost. Further, *B. tabaci* has evolved resistance to insecticides resulting from over-reliance and use of the insecticides. For example, in 2010, different *B. tabaci* populations in various regions of China developed moderate to high levels of resistance to neonicotinoids, such as the resistance to imidacloprid increasing by 28-1900 times, and the resistance to thiamethoxam increasing by 29-1200 times. By 2018, the resistance of *B. tabaci* to thiamethoxam has increased by 192-1040 times.

Genetic engineering of crops for improving insect resistance is the most economical and effective method in integrated control of agricultural pests. However, there are still many unknown fields to be explored in the study of *B. tabaci* resistance-related genes. As moving into the post-genomic era, functional genomic research has become the frontier of life science.

*Arabidopsis thaliana* is considered as a model plant, because it has relatively easy transgenic approaches, and has collinearity with the genome of other dicotyledon-type plants. The research on *A. thaliana* has great reference and practical significance for social-economic development and biological studies. Now, the detailed genetic and physical maps of *A. thaliana* genome have been completed, which lay a solid foundation for further studying on functional genes by using *A. thaliana* as a model plant. It also has great significance for developing new crop varieties with high resistance to pests, by using *A. thaliana* as a model plant to screen and study resistant genetic materials, find new resistance-related genes, and achieve mapping and cloning of such genes Lectin receptor-like kinases (LecRKs) belong to a class of subfamilies of receptor-like kinases in plants, and play important roles in plant physiological reactions, such as regulating growth and development, and protecting against pathogens. LecRKs can perceive different external stimulus mainly through extracellular domains, and convert extracellular signals to intracellular signals through intracellular kinase properties, so as to regulate cellular physiological and biochemical reactions. By now, 75 members of LecRKs have been found in *A. thaliana*, and can be divided into three categories: 32 G-type, 1 C-type and 42 L-type LecRKs. Among them, the G-type LecRKs play an important role in self-incompatibility. The C-type LecRKs are $Ca^{2+}$-dependent proteins, exist extensively in mammals, and involve in pathogen recognition and immune responses. However, the C-type LecRKs are rare in plants, and only one C-type LecRK was found in *A. thaliana*. The L-type LecRKs were named for the extreme similarity of its extracellular receptor domain with soluble lectin proteins, which are ubiquitous in leguminous seeds. While, very little is known about the L-type LecRKs.

In LecRKs gene family, the promoter region of LecRK-IX.1 (At5g10530) contains cis-regulatory elements, such as light-, ABA-, GA-, drought-, heat shock-, damage-, anaerobic-, activator-, endosperm expression-, lactose expression-, zein-responsive elements. However, there is no defense- and stress responsive element, which indicates that LecRK-IX.1 has no active defense or stress response. The expression of LecRK-IX.1 (At5g10530) has little variations at different growth stages of *A. thaliana*, and maintains at a low level. It indicates that this gene may be induced by some factors, especially by pathogens or adverse situations, and thus has a potential to be a disease-resistant gene. It has been reported that *Arabidopsis* shows *Phytophthora* resistance when LecRK-IX.1 (At5g10530) is highly expressed, which further implies that LecRK-IX.1 (At5g10530) is a disease resistant gene.

SUMMARY

One objective of the present disclosure is to provide a protein for regulating insect resistance of *Arabidopsis thaliana*, and its encoding gene and uses thereof.
In the first aspect, the present disclosure provides use of a lectin receptor-like kinase LecRK-IX.1 as a protein for regulating insect resistance of *A. thaliana*.

Further, the insect resistance refers to resistance to *Bemisia tabaci*.

In the second aspect, the present disclosure provides use of a gene AT5G10530 encoding a lectin receptor-like kinase LecRK-IX.1, as a gene for regulating insect resistance of *A. thaliana*.

Further, the insect resistance refers to resistance to *B. tabaci*.

In the third aspect, the present disclosure provides a method of increasing insect resistance of *A. thaliana*, including a step of reducing an expression of a lectin receptor-like kinase LecRK-IX.1 in *A. thaliana*.

Further, the insect resistance refers to resistance to *Bemisia tabaci*.

Further, the expression of the lectin receptor-like kinase LecRK-IX.1 may be reduced by knocking out, or reducing the expression of, a gene AT5G10530 encoding the lectin receptor-like kinase LecRK-IX.1.

In the fourth aspect, the present disclosure provides a breeding method of insect-resistant *A. thaliana*, including a step of reducing an expression of a lectin receptor-like kinase LecRK-IX.1 in *A. thaliana*, so as to increase insect resistance of *A. thaliana*.

Further, the insect resistance refers to resistance to *B. tabaci*.

Further, the expression of the lectin receptor-like kinase LecRK-IX.1 may be reduced by knocking out, or reducing the expression of, a gene encoding the lectin receptor-like kinase LecRK-IX.1.

The present disclosure has the following beneficial effects:

The present disclosure relates to use of the lectin receptor-like kinase LecRK-IX.1 as a protein for regulating insect resistance of *A. thaliana*. It allows insect-sensitive *A. thaliana* to have high resistance to *Bemisia tabaci* by reducing, or knocking out the expression of, the gene encoding the lectin receptor-like kinase LecRK-IX.1. Therefore, *A. thaliana* with high resistance to *B. tabaci* can be cultivated, and the above gene and encoded protein thereof can be applied to plant genetic improvement.

DETAILED DESCRIPTION

Hereinafter, the present disclosure will be illustrated in detail with reference to the examples. It should be appreciated that the following examples are only intended to further explain the present disclosure, but not to limit the protective scope thereof. Any improvements and adjustments made by those skilled in the art based on the principles of the present disclosure shall fall into the protective scope thereof. The specific process parameters given in the following examples are illustrated examples in an appropriate range. That is, those skilled in the art can make any appropriate choice within the range described in the present disclosure, rather than being limited to the specific data as shown in the followings.

Example 1

With gene editing technology, AT5G10530 gene is knocked out in a gene knockout experiment, to make insect-sensitive *A. thaliana* have high resistance to *B. tabaci*.

The sequence of AT5G10530 is as follows:

(SEQ ID NO: 1)
ATGGCCAACTCAATTCTGTTATTTTCCTTTGTTTTGGTTCTCCCTTTTGT

CTGTTCAGTTCAATTTAACATATCTCGTTTTGGATCAGATGTTTCTGAAA

TAGCATACCAAGGAGATGCAAGAGCAAATGGGGCTGTTGAGCTTACCAAC

ATTGACTACACATGCCGTGCCGGTTGGGCTACTTATGGTAAGCAGGTTCC

TTTATGGAATCCAGGTACCAGTAAGCCTTCGGATTTTAGTACGCGTTTCT

CCTTCAGAATTGATACCCGTAATGTTGGGTATGGTAATTACGGTCATGGG

TTTGCTTTCTTTCTAGCTCCAGCGAGAATCCAATTGCCTCCCAACTCAGC

TGGTGGTTTCTTGGGTCTATTCAATGGAACCAATAATCAGTCTTCTGCTT

-continued

```
TCCCACTTGTTTATGTCGAGTTCGACACATTTACTAATCCAGAATGGGAT

CCTCTCGATGTCAAATCCCATGTAGGAATCAACAACAACTCTCTTGTTTC

TTCTAACTACACTTCTTGGAATGCAACGTCACACAACCAAGATATAGGCC

GTGTCCTGATATTCTATGATTCCGCTAGAAGAAACTTGAGTGTCTCTTGG

ACTTACGACTTAACATCTGATCCTCTGGAGAATTCAAGCCTATCTTACAT

CATTGATCTCTCAAAGGTACTGCCATCAGAAGTTACAATTGGGTTTTCTG

CGACATCTGGAGGGGTCACCGAGGGAAATAGACTTCTGTCATGGGAGTTC

AGTTCAAGCCTGGAGCTAATAGATATAAAGAAAAGTCAGAATGACAAGAA

GGGGATGATAATTGGTATTTCAGTTTCTGGGTTCGTTTTGCTGACCTTTT

TTATTACCTCGCTCATCGTCTTCTTGAAACGGAAGCAGCAGAAGAAGAAA

GCAGAGGAGACAGAAAACTTAACATCGATAAATGAAGATCTCGAAAGAGG

AGCAGGACCAAGAAAGTTTACTTATAAAGATCTTGCATCAGCTGCAAACA

ATTTCGCAGATGATAGGAAGCTAGGGGAAGGAGGGTTTGGAGCGGTTTAT

AGAGGGTACTTAAACAGCTTAGATATGATGGTTGCGATAAAGAAGTTTGC

GGGTGGGTCTAAGCAGGGAAAAAGAGAGTTCGTAACCGAAGTAAAGATAA

TCAGCAGTTTGAGACATCGAAACCTTGTGCAACTCATTGGTTGGTGCCAT

GAGAAAGATGAGTTTCTAATGATATACGAGTTCATGCCAAATGGTAGCCT

TGACGCCCATCTATTTGGTAAAAAGCCGCATCTCGCTTGGCATGTGAGAT

GCAAAATAACTCTCGGTCTCGCCTCTGCACTGCTTTATCTTCACGAGGAG

TGGGAGCAGTGTGTTGTACACAGAGACATCAAGGCGAGTAATGTGATGCT

CGACTCCAATTTCAATGCCAAGCTTGGTGATTTCGGGTTGGCTAGATTGA

TGGACCACGAGCTAGGTCCACAGACTACAGGGTTAGCAGGAACATTTGGT

TACATGGCTCCTGAATACATAAGCACCGGAAGGGCGAGCAAAGAATCTGA

TGTGTATAGCTTTGGAGTGGTTACATTAGAGATTGTTACAGGAAGAAAAT

CTGTGGATCGAAGACAAGGAAGAGTAGAGCCTGTAACAAACCTTGTAGAG

AAAATGTGGGACCTTTATGGAAAAGGAGAAGTTATTACAGCTATCGACGA

GAAACTCAGGATCGGTGGTTTCGATGAGAAACAAGCAGAATGTCTCATGA

TTGTAGGATTATGGTGTGCTCATCCTGATGTAAACACGAGGCCTTCAATA

AAACAAGCAATCCAAGTCTTGAATCTTGAAGCACCAGTGCCTCATCTTCC

GACCAAAATGCCTGTCGCAACATATCATGTATCCTCTTCGAATACTACAT

CGGTAAGCTCTGGTGGAGCTACGGTAACGTTTTCAAGTGCTCAACATGGT

CGTTGA.
```

1. Construction of a Knock-Out Vector for a Gene of *A. thaliana*

According to the cDNA sequence of AT5G10530 gene, the 5'-end fragment was selected as a target sequence, and a gRNA (guide RNA) sequence was designed and synthesized. The target and corresponding gRNA sequences are shown below, but not limited thereto. The gRNA sequence fragments are reassembled into a H2S-cas9pl(AT) vector containing a hygromycin (Hyg) resistant tag. One or more nucleotides were mutated in the target sequence, that is not divisible by three, by means of the CRISPR/Cas9 genome-editing vector system to delete or insert nucleotide(s) in the target sequence. As a result, the cDNA sequence of AT5G10530 gene had a frameshift mutation, and produced a different amino acid product from the original one. That is, the AT5G10530 gene was knocked out.

```
gRNA sequence 1:
                                    (SEQ ID NO: 2)
    5'-TCCGAAGGCTTACTGGTACC-3';;

Target sequence 1:
                                    (SEQ ID NO: 3)
    5'-TCCGAAGGCTTACTGGTACCTGG-3'..
```

2. Obtain *A. thaliana* Knockout Seedlings Through Genetic Transformation

1) Induce calluses by using mature embryos of insect-sensitive *A. thaliana* as raw materials: Take cultured EHA105 *Agrobacterium* solution and place it in a centrifuge tube, centrifugate and pipette supernatant, to make *Agrobacterium* suspension. Select calluses of a certain size, infect with the *Agrobacterium* suspension, and place the infected callus on a co-cultivation medium.

2) Screen: Take out the infected calluses, air dry, and then transfer the calluses to a screening medium for a first screening process. Transfer initial calluses with resistant calluses to a new screening medium for a second screening process.

3) Induce the differentiation and rooting of the resistant calluses. Pick up the resistant calluses, and transfer to a petri dish with a differentiation medium, seal with Parafilm, and incubate in a constant temperature incubator to differentiate into seedlings. Move the seedlings of about 1 cm to a rooting medium in order to obtain strong seedlings.

4) PCR detection of the Hyg-resistant gene. Detect the presence of the Hyg-resistant gene in *A. thaliana* seedlings by a conventional PCR amplification method using specific primers of the Hyg-resistant gene. If the resistant gene is detected, the corresponding *A. thaliana* seedlings would be positively transformed seedlings.

Specific Primers of the Resistant Genes:

```
Hyg-f:
                                    (SEQ ID NO: 4)
    5'-ACGGTGTCGTCCATCACAGTTTGCC-3',,

Hyg-r:
                                    (SEQ ID NO: 5)
    5'-TTCCGGAAGTGCTTGACATTGGGA-3'.,
```

5) Knock-out test for positive seedlings. Design detection primers targeting near the target sequence to perform PCR application reactions, then sequence the PCR products, and determine whether the target gene was knocked out (or whether a homozygous knockout seedling was obtained). Finally, the seedlings, which were homozygous for the knocked out AT5G10530 gene, were successfully obtained from *B. tabaci*-sensitive *A. thaliana*.

3. Identification of Insect Resistance of Knockout Seedlings of *A. thaliana*

The seedlings, which were homozygous for the knocked out AT5G10530 gene, of insect-sensitive *A. thaliana*, were tested for their resistance to *B. tabaci*. It was demonstrated that these homozygous seedlings having knockout of AT5G10530 gene had strong resistance to *Bemisia tabaci* with Antibiosis Scores between 30 and 45. Antibiosis Score is one of the parameters for judging the antibiosis level of a plant, and a plant is considered to be a high-resistant variety when it has an Antibiosis Score of less than 60. Thus, the result indicated that the insect-sensitive *A. thaliana* was conferred with high insect resistance by knocking out AT5G10530 gene.

The invention claimed is:

1. A method of increasing insect resistance of an *Arabidopsis thaliana* plant, wherein the method comprises
   introducing into an *Arabidopsis thaliana* cell a Cas9 endonuclease and a gRNA comprising SEQ ID NO:2 so as to generate a knockout mutation in SEQ ID NO:1; and
   regenerating a plant from the knocked-out cell.

* * * * *